(12) United States Patent
Yamamoto et al.

(10) Patent No.: US 8,563,751 B2
(45) Date of Patent: Oct. 22, 2013

(54) METHOD FOR MANUFACTURING TRIMELLITIC ANHYDRIDE ARYL ESTER

(75) Inventors: Tomoya Yamamoto, Wakayama (JP); Seiji Kawano, Wakayama (JP); Kouji Muragaki, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/140,564

(22) PCT Filed: Dec. 22, 2009

(86) PCT No.: PCT/JP2009/071299
§ 371 (c)(1),
(2), (4) Date: Aug. 31, 2011

(87) PCT Pub. No.: WO2010/074065
PCT Pub. Date: Jul. 1, 2010

(65) Prior Publication Data
US 2012/0029215 A1 Feb. 2, 2012

(30) Foreign Application Priority Data
Dec. 22, 2008 (JP) ................ 2008-325951

(51) Int. Cl.
C07D 307/89 (2006.01)
C07D 407/10 (2006.01)

(52) U.S. Cl.
USPC .......................... 549/244; 549/252

(58) Field of Classification Search
USPC ................ 549/244, 252
See application file for complete search history.

(56) References Cited

U.S. PATENT DOCUMENTS 3,784,573 A 1/1974 Fields et al.
4,672,105 A 6/1987 Schlosser et al.

FOREIGN PATENT DOCUMENTS

| JP | 61-56155 A | 3/1986 |
|----|------------|--------|
| JP | 2-172946 A | 7/1990 |
| JP | 7-41472 A | 2/1995 |
| JP | 8-53436 A | 2/1996 |
| JP | 2000-191590 A | 7/2000 |
| JP | 2000-296047 A | 10/2000 |
| JP | 2006-206486 A | 8/2006 |

OTHER PUBLICATIONS

D. F. Loncrini, "Aromatic Polyesterimides," Journal of Polymer Science Part A-1; Polymer Chemistry, vol. 4, No. 6, Jun. 1, 1966, pp. 1531-1541.

Zhang D et al., "Transesterification of Ethylene Carbonate with Dimethyl Terephthalate over Various Metal Acetate Catalysts," Chemical Research in Chinese Universities, Beijing, CN, vol. 23, No. 2, Mar. 1, 2007, pp. 173-175.

The extended European search report issued by European Patent Office in the corresponding European patent application No. 09834866.7 on May 25, 2012.

*Primary Examiner* — Taylor Victor Oh
(74) *Attorney, Agent, or Firm* — Knobbe, Martens, Olson & Bear LLP

(57) ABSTRACT

Disclosed is a method for manufacturing a trimellitic anhydride aryl ester in an efficient, high-yielding manner, wherein carboxylic acid lithium salt is used as a catalyst when a carboxylic acid aryl ester and trimellitic anhydride are caused to undergo an ester exchange reaction to manufacture a trimellitic anhydride aryl ester.

7 Claims, No Drawings

METHOD FOR MANUFACTURING TRIMELLITIC ANHYDRIDE ARYL ESTER

TECHNICAL FIELD

The present invention relates to a method for manufacturing a trimellitic anhydride aryl ester. Specifically, the present invention relates to a method for manufacturing a trimellitic anhydride aryl ester in an efficient, high-yielding manner.

PRIOR ART

A trimellitic anhydride aryl ester is useful as a material for polyester imide resins and other heat-resistant resins as well as a curing agent or modifier for epoxy resins and urethane resins.

Several conventional methods are known for manufacturing a trimellitic anhydride aryl ester. For example, a method is know whereby trimellitic anhydride halide is caused to react with divalent aromatic diol, in the presence of amine, in a mixed solution constituted by aliphatic ketone and aromatic hydrocarbon (Patent Literature 1). However, trimellitic anhydride halide, which is used as one of the materials under this method, is expensive and the obtained trimellitic anhydride ester may contain halogen-containing impurities derived from acid halide, which limits the use of this trimellitic anhydride ester depending on the application. Another known method is one whereby a phenolic acetic acid ester and trimellitic anhydride are caused to undergo an ester exchange reaction in the presence of a phase transfer catalyst (Patent Literature 2), but this method does not offer sufficient reaction speed and reaction selectivity.

Another method is known whereby a phenolic acetic acid ester is caused to react with trimellitic anhydride in the presence of a silica/alumina catalyst, or inorganic compound catalyst constituted by alkali metal or alkali earth metal (Patent Literature 3). However, any such inorganic compound constituted by alkali metal or alkali earth metal does not offer sufficient reaction speed and reaction selectivity, and a silica/alumina catalyst does not offer sufficient reaction speed and reaction selectivity and the catalyst itself is also expensive.

Yet another method is known whereby a phenolic acetic acid ester and trimellitic anhydride are caused to undergo an ester exchange reaction in the presence of a sodium acetate catalyst (Patent Literature 4), but this method does not offer sufficient reaction speed and reaction selectivity.

Patent Literature 1: Japanese Patent Laid-open No. Hei 08-053436
Patent Literature 2: Japanese Patent Laid-open No. 2006-206486
Patent Literature 3: Japanese Patent Laid-open No. Hei 07-041472
Patent Literature 4: U.S. Pat. No. 3,784,573

SUMMARY OF THE INVENTION

Problems to be Solved by the Invention

In light of the aforementioned situations concerning the conventional methods for manufacturing a trimellitic anhydride ester, the object of the present invention is to provide a method for manufacturing the target substance, or specifically a trimellitic anhydride aryl ester, under conditions that can be achieved easily in industrial settings in a manner preventing mixing-in of halogen-containing impurities derived from trimellitic acid halide and also ensuring good efficiency as well as high selectivity and yield achieved over a short reaction time.

Means for Solving the Problems

After conducting earnest studies to achieve the aforementioned object, the inventors of the present invention found that, by using a carboxylic acid aryl ester and trimellitic anhydride as materials and causing them to undergo an ester exchange reaction using carboxylic acid lithium salt as a catalyst, the target trimellitic anhydride aryl ester would be obtained with higher selectivity and yield over a shorter reaction time compared to when an ester exchange reaction of a carboxylic acid aryl ester and trimellitic anhydride was implemented using known catalysts, and subsequently completed the present invention. In other words, the present invention provides a method for manufacturing a trimellitic anhydride aryl ester characterized in that carboxylic acid lithium salt is used as a catalyst to implement an ester exchange reaction of a carboxylic acid aryl ester and trimellitic anhydride.

Effects of the Invention

According to the method for manufacturing a trimellitic anhydride aryl ester proposed by the present invention, which is a method to cause a carboxylic acid aryl ester and trimellitic anhydride to undergo an ester exchange reaction by using, as a catalyst, carboxylic acid lithium salt of an amount in a specified range, the reaction speed and/or reaction selectivity (yield of target substance) will improve significantly compared to when sodium acetate, which is also a known alkali metal salt, or other catalysts are used to manufacture a trimellitic anhydride aryl ester, and consequently the target substance can be obtained with high purity and greater ease in industrial settings.

BEST MODE FOR CARRYING OUT THE INVENTION

The method for manufacturing a trimellitic anhydride aryl ester proposed by the present invention is characterized in that carboxylic acid lithium salt is used as a catalyst in the ester exchange reaction of a carboxylic acid aryl ester and trimellitic anhydride.

In the aforementioned manufacturing method, the target trimellitic anhydride aryl ester is expressed by General Formula (1) shown below:

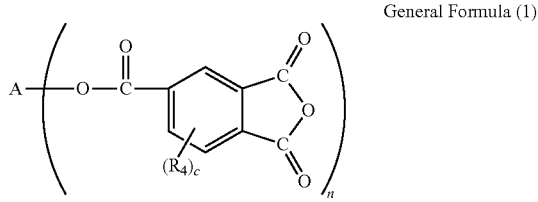

General Formula (1)

(In the formula, A represents an n-valent aromatic group, $R_4$ represents an alkyl group, alkoxyl group or phenyl group, c represents 0 or an integer of 1 to 3, and n represents an integer of 1 to 4.)

In the formula, A represents an n-valent mononuclear or polynuclear aromatic group. Specifically, A represents the residue of a phenyl nucleus obtained by removing n number of phenolic hydroxyl groups. The phenyl nucleus may be of monocyclic type such as a benzene ring, fused polycyclic type such as a naphthalene ring or fluorene ring, or mononuclear or polynuclear type.

Preferably A is a monovalent, divalent or trivalent monophenyl residue, divalent, trivalent or tetravalent bisphenyl or biphenyl residue, trivalent or tetravalent trisphenyl residue, or tetravalent tetrakis phenyl residue.

More preferably A is a divalent monophenyl residue, bisphenyl residue or biphenyl residue.

Also in the formula, the alkyl group represented by $R_4$ is preferably a straight-chain or branched-chain alkyl group with 1 to 6 carbon atoms or cyclic alkyl group with 5 or 6 carbon atoms, while the alkoxyl group is preferably a straight-chain or branched-chain alkoxyl group with 1 to 6 carbon atoms or cyclic alkoxyl group with 5 or 6 carbon atoms, where specific examples include methyl, ethyl, propyl, isopropyl, isobutyl, cyclohexyl, cyclopentyl, methoxy and ethoxy, among others. These can have a substituent such as phenyl group, alkoxyl group, halogen or oxygen atom (cyclic ether group), and the phenyl group represented by $R_4$ may also have been substituted by around one to three alkyl groups and/or alkoxyl groups with 1 to 4 carbon atoms.

Under the manufacturing method proposed by the present invention, a carboxylic acid aryl ester, which is one of the materials from which to make the aforementioned trimellitic anhydride aryl ester, is not limited in any manner as long as it has a carboxylic acid ester group that can undergo an ester exchange reaction with trimellitic anhydride under the manufacturing method proposed by the present invention, such as one expressed by General Formula (2) shown below:

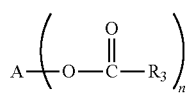

General Formula (2)

(In the formula, A and n represent the corresponding items in General Formula (1), respectively, while $R_3$ represents a hydrogen atom, saturated hydrocarbon group or phenyl group.)

In the formula, the saturated hydrocarbon group represented by $R_3$ is a straight-chain, branched-chain or cyclic saturated hydrocarbon group, where such saturated hydrocarbon group may have been substituted by a phenyl group or it may have an ether group substituted by a methoxy or other alkoxyl group.

In the case of a straight-chain or branched-chain saturated hydrocarbon group, the number of carbon atoms is preferably 1 to 10 or more preferably 1 to 4, while, in the case of a cyclic saturated hydrocarbon group, the number of carbon atoms is preferably 5 to 10 or more preferably 5 or 6. Straight-chain, branched-chain and cyclic primary or secondary alkyl groups are preferable, where specific examples include methyl group, ethyl group, propyl group, n-butyl group, t-butyl group, cyclohexyl group and benzyl group, among others. In addition, the phenyl group may be of monocyclic type such as a benzene ring or fused polycyclic type such as a naphthalene ring or fluorene ring, and the phenyl group may have been substituted with an alkyl group or alkoxyl group. With regard to $R_3$, however, it is desirable from the operational viewpoint of reaction that the boiling point of a carboxylic acid ($R_3$COOH) constituted by the $R_3$ group dissociated/generated through the ester exchange reaction and a carboxyl group bonded to it be lower than that of trimellitic anhydride, and accordingly $R_3$ does not ideally have too many carbon atoms.

The method for manufacturing such a carboxylic acid aryl ester is not limited in any manner, and any known method for manufacturing a phenolic carboxylic acid ester can be used, such as a method to use an excess amount of carboxylic acid anhydride such as acetic acid anhydride and e.t.c. to produce an ester of a carboxylic acid such as acetic acid, or method to cause carboxylic acid or halogenated acyl to react in the presence of an esterifying catalyst such as sulfuric acid or p-toluene sulfonic acid.

Specifically, it can be obtained by using, as materials, a carboxylic acid such as carboxylic acid anhydride, carboxylic acid or halogenated acyl expressed by any one of General Formulas (3) to (5) shown below and an aromatic hydroxy expressed by General Formula (6) shown below, under any known esterification method:

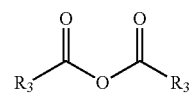

General Formula (3)

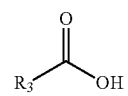

General Formula (4)

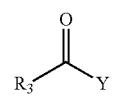

General Formula (5)

(In the formula, $R_3$ represents the corresponding item in General Formula (2), while Y represents a halogen atom.)

General Formula (6)

(In the formula, A and n represent the corresponding items in General Formula (1).)

The aromatic hydroxy expressed by General Formula (6) is preferably a monophenyl with a hydroxy group substitution number n of 1 to 3, bisphenyl or biphenyl with n of 2 to 4, trisphenyl with n of 3 or 4, or tetrakis phenyl with n of 4, among which a monophenyl with n of 2 and bisphenyl or biphenyl with n of 2 to 4 are more preferable. Among these, a monophenyl, bisphenyl or biphenyl with n of 2, or specifically a benzene diol, bisphenol or biphenol, is most preferable, which is expressed, for example, by General Formula (7) shown below:

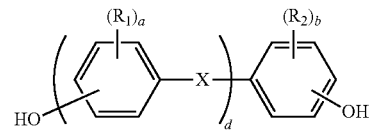

General Formula (7)

(In the formula, $R_1$ and $R_2$ each independently represent an alkyl group, alkoxyl group, aromatic hydrocarbon group or halogen group, a and b each independently represent 0 or an integer of 1 to 4, d represents 0 or an integer of 1, and X represents a single bond or divalent bonding group.)

In the above formula, the alkyl group represented by $R_1$ or $R_2$ is preferably a straight-chain or branched-chain alkyl group with 1 to 10 carbon atoms or cyclic alkyl group with 5 to 10 carbon atoms, where specific examples include methyl, ethyl, propyl, isopropyl, sec-butyl, t-butyl, isobutyl, cyclohexyl and cyclopentyl, among others. These alkyl groups may have a substituent such as phenyl group, alkoxyl group, halogen or oxygen atom (cyclic ether group).

On the other hand, the alkoxyl group is preferably a straight-chain or branched-chain alkoxyl group with 1 to 10 carbon atoms or cyclic alkoxyl group with 5 to 10 carbon atoms, where specific examples include methoxy, ethoxy, isopropyloxy, cyclohexyloxy and cyclopentyloxy, among others. These alkoxyl groups may have a substituent such as phenyl group, alkoxyl group, halogen or oxygen atom (cyclic ether group).

Also, the aromatic hydrocarbon group is preferably an aromatic hydrocarbon group with 6 to 10 carbon atoms, such as phenyl group, naphtyl group or phenyl oxy group. These aromatic hydrocarbon groups may have a substituent such as alkyl group, alkoxyl group, halogen or oxygen atom (cyclic ether group).

Furthermore, the halogen group is preferably chlorine, bromine or fluorine, among others. If a is 2 or greater, each $R_1$ may be the same or different. If b is 2 or greater, each $R_2$ may be the same or different.

As for the bonding positions of hydroxyl groups, preferable positions are 1,4 or 1,3 when d is 0, and 4,4', 2,2' or 2,4' when d is 1, where 4,4' is more preferable.

a and b each independently represent 0 or an integer of 1 to 4. They are preferably 0, 1, 2, or 3, and more preferably be 0, 1 or 2.

X represents a single bond or divalent bonding group. A preferable form of divalent bonding group is an organic group, where specific examples include oxygen atom (—O—), sulfur atom (—S—), sulfonyl group (—SO$_2$—) and carbonyl group (—CO—), among others, as well as alkylene group, aromatic hydrocarbon group which may be bonded to an alkylene group, and alkenylene group.

The alkylene group is a straight-chain, branched-chain or cyclic alkylene group, where specific examples include 1,2-ethane diyl, 1,3-propane diyl, methylene, 1,1-ethane diyl, 2,2-propane diyl, 1,1-cyclohexane diyl and 1,4-cyclohexylene, among others.

Specific examples of the aromatic hydrocarbon group include 1,4-phenylene, 1,3-phenylene, 4,4'-biphenylene and 2,2'-biphenylene, among others. These aromatic hydrocarbon groups may have a substituent such as alkyl group or alkoxyl group. Furthermore, specific examples of the aromatic hydrocarbon group which may be bonded to an alkylene group include 1,3-isopropylbenzene-α,α'-diyl, 1,4-isopropylbenzene-α, α'-diyl and 1,4-dimethylbenzene-α,α'-diyl, among others.

Specific examples of the alkenylene group include vinylene, among others.

Specific examples of these aromatic diols expressed by General Formula (7) include 4,4'-biphenol, 3,3'-dimethyl-4,4'-biphenol, bis(4-hydroxyphenyl)methane, 2,2-bis(4-hydroxyphenyl)propane, 1,1-bis(4-hydroxyphenyl)ethane, 1,1-bis(4-hydroxyphenyl)cyclohexane, 1,1-bis(4-hydroxyphenyl)-3,3,5-trimethylcyclohexane, 9,9-bis(4-hydroxyphenyl)fluorene, 3-methyl-4,4''-dihydroxy-p-terphenyl, 3-isopropyl-4,4''-dihydroxy-p-terphenyl, 3,5-dimethyl-4,4''-dihydroxy-p-terphenyl, 3,3'''-dimethyl-4,4'''-dihydroxy-p-quarterphenyl, 3,3'''-diisopropyl-4,4'''-dihydroxy-p-quarterphenyl, 1,4-bis{1-(4-hydroxyphenyl)isopropyl}benzene, 1,3-bis{1-(4-hydroxyphenyl)isopropyl}benzene, 4,4'-dihydroxy diphenylether, 4,4'-dihydroxybenzophenone, 4,4'-dihydroxydiphenylsulfone, 3,3'-diphenyl-4,4'-biphenol, 1-(3-methyl-4-hydroxyphenyl)-4-(4-hydroxyphenyl)-1-cyclohexene, 4,4'-di(4-hydroxyphenyl)-1,1'-bicyclohexane-3,3'-diene, 4,4'-di (3-methyl-4-hydroxyphenyl)-1,1'-bicyclohexane-3,3'-diene, hydroquinone and resorcin, among others.

In other words, the carboxylic acid aryl ester expressed by General Formula (2), which is obtained from the aromatic diol expressed by General Formula (7) and carboxylic acid expressed by, for example, any one of General Formulas (3) to (5), is expressed by General Formula (8) shown below, for example:

General Formula (8)

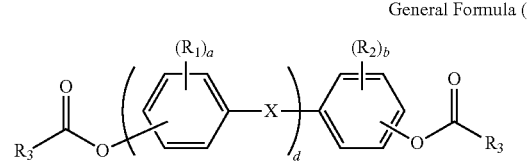

(In the formula, $R_1$, $R_2$, a, b, d and X represent the corresponding items in General Formula (7), while $R_3$ represents the corresponding item in General Formula (2).)

Also, the trimellitic anhydride is expressed by General Formula (9) shown below, for example:

General Formula (9)

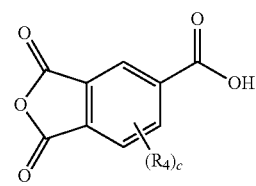

(In the formula, $R_4$ and c represent the corresponding items in General Formula (1).)

In General Formula (9) shown above, the alkyl group, alkoxyl group or phenyl group represented by $R_4$ is specifically the same as the alkyl group, alkoxyl group or phenyl group represented by $R_4$ in General Formula (1). Also, c is preferably 0. In other words, a preferable form of trimellitic anhydride expressed by General Formula (9) is trimellitic anhydride (non-substituted form).

In other words, the trimellitic anhydride aryl ester expressed by General Formula (1), which is obtained from the carboxylic acid aryl ester expressed by General Formula (8) above and trimellitic anhydride expressed by General Formula (9) above according to the manufacturing method proposed by the present invention, is expressed by General Formula (10) shown below, for example:

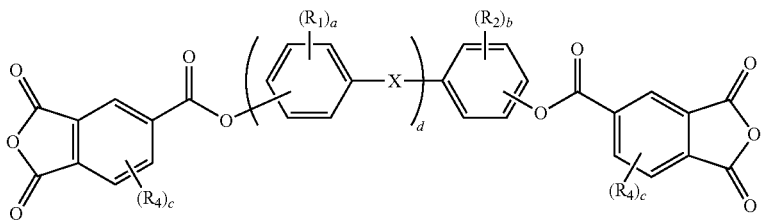

General Formula (10)

(In the formula, $R_1$, $R_2$, a, b, d and X represent the corresponding items in General Formula (7), while $R_4$ and c represent the corresponding items in General Formula (1).)

Under the method for manufacturing a trimellitic anhydride aryl ester proposed by the present invention, a carboxylic acid aryl ester and trimellitic anhydride are used as materials and when they are caused to undergo an ester exchange reaction, carboxylic acid lithium salt is used as a catalyst. For the carboxylic acid constituting this carboxylic acid lithium salt, an aliphatic monocarboxylic acid, aromatic monocarboxylic acid, aliphatic polyvalent carboxylic acid or aromatic polyvalent carboxylic acid can be used, among others. A monocarboxylic acid or dicarboxylic acid is a preferable form of carboxylic acid component, where monocarboxylic acid is more preferable.

The number of carbon atoms of carboxylic acid (including carbons in the carboxylic acid) is preferably 1 to 30, or more preferably 1 to 10, or most preferably 1 to 5.

Examples of hydrocarbon groups constituting the groups that are left after the carboxyl group has been removed from the carboxylic acid include straight-chain, branched-chain or cyclic saturated hydrocarbon groups, unsaturated hydrocarbon groups and aromatic hydrocarbon groups, where these hydrocarbon groups may have a substituent such as aliphatic group or aromatic group.

In other words, specific examples of carboxylic acid lithium salt include, among others: saturated aliphatic monocarboxylic acid lithium salt such as lithium formate, lithium acetate, lithium propionate, lithium butanoate, lithium pentanoate, lithium hexanoate, lithium stearate and lithium cyclohexane carboxylate; unsaturated aliphatic monocarboxylic acid lithium salt such as lithium acrylate or lithium crotonate; saturated aliphatic dicarboxylic acid lithium salt such as lithium oxalate, lithium maronate, lithium succinate, lithium glutarate or lithium adipate; unsaturated aliphatic dicarboxylic acid lithium salt such as lithium maleate or lithium fumarate; aromatic monocarboxylic acid lithium salt such as lithium benzoate or lithium naphthoate; and aromatic dicarboxylic acid lithium salt such as lithium phthalate or lithium terephthalate. Among these, saturated aliphatic monocarboxylic acid lithium salt or saturated aliphatic dicarboxylic acid lithium salt is a preferable form of saturated aliphatic carboxylic acid lithium salt, where saturated aliphatic monocarboxylic acid lithium salt is more preferable.

The number of carbon atoms of saturated aliphatic carboxylic acid lithium salt (including carbons in the carboxylic acid) is preferably 1 to 30, or more preferably 1 to 10, or most preferably 1 to 5.

In other words, saturated aliphatic monocarboxylic acid lithium salt with 1 to 5 carbon atoms (including carbons in the carboxylic acid), such as lithium acetate or lithium propionate, is most preferable.

Under the manufacturing method proposed by the present invention, the amount of carboxylic acid lithium salt used is preferably in a range of 0.005 to 10 mol percent, or more preferably in a range of 0.01 to 5 mol percent, or most preferably in a range of 0.05 to 3 mol percent, relative to the ester group in the material carboxylic acid aryl ester. Here, mol percent is a value defined by the expression, "Mol percent= (Number of catalyst mols/Number of ester group mols)× 100." The number of ester group mols is obtained by the expression, "Number of material carboxylic acid aryl ester mols×Number of ester group in the molecule."

In other words, the amount is preferably in a range of 0.01 to 20 mol percent, or more preferably in a range of 0.02 to 10 mol percent, or most preferably in a range of 0.1 to 6 mol percent, relative to the carboxylic acid aryl ester expressed by General Formula (8).

By using carboxylic acid lithium salt by an amount in these ranges, the ester exchange reaction of a carboxylic acid aryl ester and trimellitic anhydride can be concluded over a short period at high selectivity and high yield.

Also under the manufacturing method proposed by the present invention, the amount of trimellitic anhydride used is normally at least 1, or preferably a range of 1 to 5, or more preferably a range of 1.3 to 1.7 times, in mol, the amount of the ester group in the carboxylic acid aryl ester. Here, the "time in mol" used to calculate the amount of trimellitic anhydride used relative to the ester group is obtained by the expression, "Number of trimellitic anhydride mols/Number of ester group mols."

In other words, the amount of trimellitic anhydride used is normally at least 2, or preferably a range of 2 to 10, or more preferably a range of 2.6 to 3.4 times, in mol, the amount of the carboxylic acid aryl ester expressed by General Formula (8).

The temperature of the ester exchange reaction is normally in a range of 100 to 300° C., or preferably in a range of 150 to 250° C., or more preferably in a range of 200 to 230° C.

Under the manufacturing method proposed by the present invention, use of reaction solvent is desirable for such reasons as improving the operability in industrial production and raising the reaction speed.

The solvent used is not limited in any manner as long as it is not distilled from the reaction container at the above reaction temperatures and remains inert during the ester exchange reaction. Specific examples include, among others: aromatic hydrocarbon ether solvent such as phenetole, butylphenylether or other alkyl aryl ether, or diphenyl ether, di-p-triyl ether or other diaryl ether; biphenyl, terphenyl or other aromatic hydrocarbon solvent; diisopropylnaphthalene or other alkyl substituted naphthalene, decalin, kerosene or other aliphatic hydrocarbon, tetraethyleneglycoldimethyl ether, diethyleneglycoldibutyl ether or other polyalkyleneglycol ether; or Therm S Series (manufactured by Nippon Steel Chemical), KSK-OIL Series (manufactured by Soken Chemical & Engineering), Neo SK-OIL Series (manufactured by Soken Chemical & Engineering) or other organic heating medium.

If a solvent is used, its amount is normally in a range of 1 to 10 parts by weight, or preferably in a range of 2 to 3 parts by weight, relative to 1 part by weight of the material carboxylic acid aryl ester.

Under these reaction conditions, the reaction normally concludes in around 1 to 28 hours, or preferably in around 4 to 7 hours.

Also, it is desirable that generated carboxylic acid be distilled during the reaction, which means that the carboxylic acid generated through the ester exchange reaction is desirably a carboxylic acid whose boiling point is lower than that of material trimellitic anhydride.

The reaction may be implemented at normal pressure or under compression or decompression, but preferably it is implemented at normal pressure or under decompression. This can be achieved by, for example, adjusting the reaction pressure according to the boiling point of the generated carboxylic acid.

The reaction method is not limited in any manner, and it is possible, for example, to introduce the material carboxylic acid aryl ester, trimellitic anhydride and carboxylic acid lithium salt, and solvent, in a reaction container in an inert ambience, and then heat the mixture under agitation, to conclude the reaction by distilling the generated carboxylic acid. When the reaction is complete, the target substance can be separated and refined from the reaction solution by any known method. For example, the reaction solution can be cooled directly or mixed with a poor solvent and then cooled, after which the precipitated crystal can be filtered out to obtain the target substance at low to high purity. If necessary, thus obtained substance can be crystallized/filtered again to make it purer.

It is also possible to obtain the target substance at high purity where the content of metals such as inorganic salt is reduced by, for example, filtering the solvent in which the target substance is dissolved to filter out inorganic salt, or washing in water, prior to the crystallization step in the above refining operation.

Upon contacting water some or all acid anhydride groups may open rings and generate carboxylic acid, but it can be returned to the target substance by, e.g., heating the carboxylic acid or causing it to react with an acid anhydride such as acetic acid anhydride.

EXAMPLES

Reference Example 1

After introducing 675.0 g (6.6 mol) of acetic acid anhydride and 342.0 g (1.5 mol) of 2,2-bis(4-hydroxyphenyl)propane into a 3-liter four-way flask equipped with a thermometer, reflux condenser and agitation blades, the mixture was heated to 130° C. under agitation and then kept at that temperature for 2.5 hours under agitation to cause reaction.

When the reaction was complete, 703 g of toluene was added and the mixture was cooled, after which water was added and the mixture was agitated and washed in water. Thereafter, the water layer was separated and removed and then toluene was distilled and removed from the obtained oil layer, after which 937 g of heptane was added and the mixture was crystallized and filtered to obtain 2,2-bis(4-hydroxyphenyl)propane diacetate (hereinafter referred to as "BPA-DA") of 99.4% in purity (according to high-speed liquid chromatography) in crystal form.

Example 1

A 300-ml four-way flask equipped with an agitator, thermometer, Dean-Stark and reflux condenser was replaced with nitrogen, after which 25.0 g (0.080 mol) of BPA-DA obtained in Reference Example 1, 46.2 g (0.241 mol) of trimellitic anhydride, 0.25 g (4.7 mol percent relative to BPA-DA) of lithium acetate and 54.5 g of diphenyl ether were introduced to the flask.

Next, the mixture was heated to 210° C. under nitrogen flows to cause reaction at 210° C. under agitation. The mixture was heated to 210° C. under nitrogen flows at normal pressure, and then kept at that temperature for 7 hours to cause reaction. During the reaction, produced acetic acid was removed by distillation as the reaction progressed. Reaction solution was sampled 4 hours and 7 hours after the mixture had been heated to 210° C., and analyzed by GPC (gel permeation chromatography).

The results are shown in Table 1.

The reaction selectivity of 2,2-bis{4-(1,3-dioxo-1,3-dihydroisobenzofuran-5-ylcarbonyloxy)phenyl}propane, which is the target substance (bistrimellitic anhydride), was 96.7%.

Example 2

Reaction was caused based on the same operation explained in Example 1, except that lithium benzoate was used, instead of lithium acetate in Example 1, by 4.7 mol percent relative to BPA-DA. The mixture was heated to 210° C. and reaction solution was sampled 4 hours and 7 hours thereafter, and analyzed by GPC. The results are shown in Table 1.

Example 3

Reaction was caused based on the same operation explained in Example 1, except that diethyleneglycoldibutyl ether was used, instead of diphenyl ether in Example 1, by 54.5 g. The mixture was heated to 210° C. and reaction solution was sampled 4 hours and 7 hours thereafter, and analyzed by GPC. The results are shown in Table 1.

Example 4

Reaction was caused based on the same operation explained in Example 1, except that liquid paraffin was used, instead of diphenyl ether in Example 1, by 54.5 g. The mixture was heated to 210° C. and reaction solution was sampled 7 hours thereafter, and analyzed by GPC. The results are shown in Table 1.

Example 5

A 300-ml four-way flask equipped with an agitator, thermometer, Dean-Stark and reflux condenser was replaced with nitrogen, after which 21.6 g (0.080 mol) of 4,4'-biphenoldiacetate, 46.1 g (0.24 mol) of trimellitic anhydride, 0.2 g (0.0030 mol) of lithium acetate and 142.6 g of diphenyl ether were introduced to the flask.

Next, the mixture was heated under nitrogen flows to cause reaction at 225 to 230° C. for 7 hours under agitation. During the reaction, produced acetic acid was removed by distillation as the reaction progressed. Reaction solution was sampled 4 hours and 7 hours after the mixture had been heated to 225° C., and analyzed by GPC. The results are shown in Table 1.

When measured after the reaction, the reaction selectivity of 4,4'-bis(1,3-dioxo-1,3-dihydroisobenzofuran-5-ylcarbonyloxy)biphenyl, which is the target substance (bistrimellitic anhydride), was 98.3%.

Comparative Example 1

Reaction was caused based on the same operation explained in Example 1, except that no catalyst was used, instead of using lithium acetate in Example 1. The mixture was heated to 210° C. and reaction solution was sampled 4 hours and 7 hours thereafter, and analyzed by GPC. The results are shown in Table 2.

Comparative Examples 2 to 9

Reaction was caused based on the same operation explained in Example 1, except that each of the catalysts listed in Table 2 was used, instead of lithium acetate in Example 1, by 0.25 g. The mixture was heated to 210° C. and reaction solution was sampled 4 hours and 7 hours thereafter, and analyzed by GPC. The results are shown respectively in Table 2.

TABLE 1

| | | GPC analysis result: Reaction selectivity (%) | | | |
|---|---|---|---|---|---|
| Catalyst | Reaction time (hrs) | Mono-ester | Target substance | Olig-omer | Reaction rate (%) |
| Example 1 Lithium acetate | 4 | 5.7 | 93.0 | 1.0 | 100 |
| | 7 | 1.5 | 96.7 | 1.8 | 100 |

TABLE 1-continued

| | | GPC analysis result: Reaction selectivity (%) | | | |
|---|---|---|---|---|---|
| Catalyst | Reaction time (hrs) | Mono-ester | Target substance | Olig-omer | Reaction rate (%) |
| Example 2 Lithium benzoate | 4 | 19.2 | 75.5 | 1.4 | 100 |
| | 7 | 6.4 | 89.7 | 2.7 | 100 |
| Example 3 Lithium acetate | 4 | 22.3 | 75.4 | 2.3 | 99.2 |
| | 7 | 9.5 | 87.3 | 3.1 | 100 |
| Example 4 Lithium acetate | 7 | 3.1 | 90.0 | 6.9 | 100 |
| Example 5 Lithium acetate | 4 | 4.2 | 94.7 | 1.1 | 100 |
| | 7 | 0.7 | 98.3 | 1.0 | 100 |

* The selectivity was calculated as an area percentage of GPC.

* Monoester refers to a compound obtained by replacing only one acetate portion of diacetate with trimellitic anhydride, and its reaction rate represents that of diacetate.

TABLE 2

| | | | GPC analysis result: Reaction selectivity (%) | | | |
|---|---|---|---|---|---|---|
| | Catalyst | Reaction time (hrs) | Monoester | Target substance | Oligomer | Reaction rate (%) |
| Comparative Example 1 | None | 4 | 67.6 | 27.9 | 4.6 | 76.5 |
| | | 7 | 47.9 | 46.0 | 5.5 | 98.0 |
| Comparative Example 2 | HSZ-500KOA (manufactured by Tosoh) | 4 | 52.4 | 15.7 | 0.5 | 68.9 |
| | | 7 | 52.1 | 32.4 | 2.7 | 86.8 |
| Comparative Example 3 | Zeolum A-3 (manufactured by Tosoh) | 4 | 47.7 | 50.2 | 1.4 | 91.6 |
| | | 7 | 19.8 | 76.9 | 2.4 | 100 |
| Comparative Example 4 | Tetraphenylphosphonium-bromide | 4 | 65.2 | 34.5 | 0.3 | 79.0 |
| | | 7 | 52.5 | 45.7 | 1.1 | 89.3 |
| Comparative Example 5 | Tetraphenylphosphoniumtetra-phenylborate | 4 | 53.4 | 37.0 | 9.7 | 88.7 |
| | | 7 | 39.7 | 47.7 | 12.2 | 98.1 |
| Comparative Example 6 | 2,4,6-trimethyl pyridinium-p-toluenesulfonate | 4 | 70.6 | 19.6 | 5.8 | 70.0 |
| | | 7 | 52.8 | 25.3 | 18.3 | 90.9 |
| Comparative Example 7 | Tetrabutylammonium hydrogen sulfate | 4 | 73.8 | 21.1 | 2.4 | 64.3 |
| | | 7 | 45.8 | 42.2 | 10.5 | 96.0 |
| Comparative Example 8 | Calcium hydroxide | 4 | 52.2 | 43.3 | 2.7 | 97.7 |
| | | 7 | 44.6 | 51.5 | 3.2 | 98.3 |
| Comparative Example 9 | Potassium hydroxide | 4 | 45.4 | 51.4 | 2.6 | 98.6 |
| | | 7 | 32.2 | 60.8 | 5.7 | 99.3 |

* The selectivity was calculated as an area percentage of GPC.

* The details of catalysts are as follows:

HSZ-500KOA

High-silica zeolite. Type L zeolite.

$SiO_2/Al_2O_3$ ratio = 6.1

$Na_2O$ = 0.24 wt %, $K_2O$ = 16.8 wt %, LOI (loss on ignition) = 8.9 wt %

Zeolum A-3

Type A zeolite.

pH12, particle size distribution = 150 mm or less, LOI = 1.8%, moisture adsorption capacity = 25%

* Monoester refers to a compound obtained by replacing only one acetate portion of diacetate with trimellitic anhydride, and its reaction rate represents that of diacetate.

According to the results of Examples and Comparative Examples, the methods used in Examples where the carboxylic acid lithium salt catalyst was used resulted in higher speeds of ester exchange reaction compared to the methods used in Comparative Examples and, given the same conditions such as solvent, these methods would produce less byproducts such as oligomer and demonstrate higher reaction selectivities of the target substance, or bistrimellitic anhydride.

What is claimed is:

1. A method for manufacturing a trimellitic anhydride aryl ester by causing a carboxylic acid aryl ester and trimellitic anhydride to undergo an ester exchange reaction, said method for manufacturing a trimellitic anhydride aryl ester characterized by using a carboxylic acid lithium salt as a catalyst.

2. A method for manufacturing a trimellitic anhydride aryl ester according to claim 1, by causing a carboxylic acid aryl ester expressed by formula (2) below and trimellitic anhydride expressed by formula (9) below to undergo an ester exchange reaction, said trimellitic anhydride aryl ester being expressed by formula (1) below:

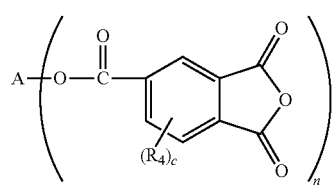

formula (1)

Wherein A represents an n-valent aromatic group, $R_4$ represents an alkyl group, alkoxy group or phenyl group, c represents 0 or an integer of 1 to 3, and n represents an integer of 1 to 4;

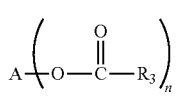

formula (2)

Wherein A and n represent the corresponding items in formula (1), while $R_3$ represents a hydrogen atom, saturated hydrocarbon group or phenyl group;

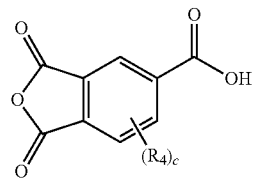

formula (9)

wherein $R_4$ and c represent the corresponding items in formula (1).

3. A method for manufacturing a trimellitic anhydride aryl ester according to claim 2, wherein n is two in formula (1) and formula (2).

4. A method for manufacturing a trimellitic anhydride aryl ester according to claim 1, by causing a carboxylic acid aryl ester expressed by formula (8) below and trimellitic anhydride expressed by formula (9) below to undergo an ester exchange reaction, said trimellitic anhydride aryl ester being expressed by formula (10) below:

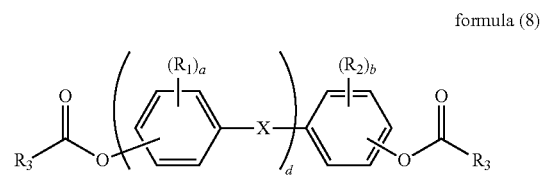

formula (8)

Wherein $R_1$ and $R_2$ each independently represents alkyl group, alkoxy group, aromatic hydrocarbon group or halogen group, a and b each independently represents 0 or an integer of 1 to 4, d represents 0 or an integer of 1, X represents a single or divalent bonding group and $R_3$ represents a hydrogen atom, saturated hydrocarbon group or phenyl group;

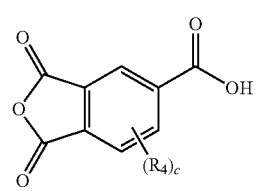

formula (9)

Wherein $R_4$ represents an alkyl group, alkoxy group or phenyl group, and c represents 0 or an integer of 1 to 3;

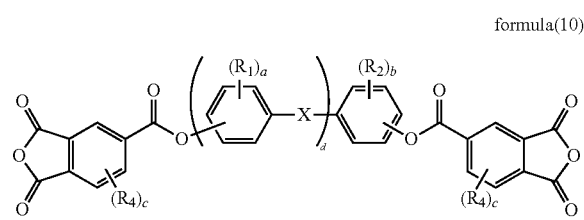

formula (10)

wherein $R_1$, $R_2$, a, b, c, d, and X represent the corresponding items in formula (8), while $R_4$ and c represent the corresponding items in formula (9).

5. A method for manufacturing a trimellitic anhydride aryl ester according to claim 1, wherein the temperature of ester exchange reaction is in a range of 150 to 250° C.

6. A method for manufacturing a trimellitic anhydride aryl ester according to claim 1, wherein the amount of trimellitic anhydride used is in a range of 1 to 5 times, in mol, the amount of the ester group in carboxylic acid aryl ester.

7. A method for manufacturing a trimellitic anhydride aryl ester according to claim 1, wherein the amount of carboxylic acid lithium salt used is in a range of 0.005 to 10 mol percent relative to the ester group in the material carboxylic acid aryl ester.

* * * * *